United States Patent

Holcomb

[11] Patent Number: 6,084,671
[45] Date of Patent: Jul. 4, 2000

[54] SURFACE ANALYSIS USING GAUSSIAN BEAM PROFILES

[76] Inventor: Matthew J. Holcomb, 3912 Ocean Dr., Manhattan Beach, Calif. 90266

[21] Appl. No.: 09/073,496

[22] Filed: May 6, 1998

Related U.S. Application Data

[60] Provisional application No. 60/045,672, May 6, 1997.

[51] Int. Cl.[7] ............... G01B 9/02; G01B 11/30; G01B 11/00
[52] U.S. Cl. ............... 356/354; 356/371; 356/359; 356/73; 356/237
[58] Field of Search ............... 356/335, 336, 356/354

[56] References Cited

U.S. PATENT DOCUMENTS

| | | | |
|---|---|---|---|
| 3,614,232 | 10/1971 | Mathisen | 356/71 |
| 4,299,443 | 11/1981 | Minami et al. | 350/162 SF |
| 4,330,775 | 5/1982 | Iwamoto et al. | 340/146.3 P |
| 4,334,780 | 6/1982 | Pernick | 356/359 |
| 4,806,774 | 2/1989 | Lin et al. | 250/550 |
| 5,155,372 | 10/1992 | Bowen et al. | 250/571 |
| 5,172,000 | 12/1992 | Scheff et al. | 250/550 |
| 5,189,481 | 2/1993 | Jann et al. | 356/73 |
| 5,488,476 | 1/1996 | Mansfield et al. | 356/354 |
| 5,506,676 | 4/1996 | Hendler et al. | 356/237 |
| 5,659,390 | 8/1997 | Danko | 356/237 |
| 5,719,405 | 2/1998 | Hayano | 250/559.41 |

*Primary Examiner*—Frank G. Font
*Assistant Examiner*—Roy M. Punnoose
*Attorney, Agent, or Firm*—Lumen Intellectual Property Services

[57] ABSTRACT

A method and apparatus for measuring the physical characteristics of reflective or transparent surfaces may be used to detect particulates, measure surface roughness, and reconstruct surface images and detect defects in regular patterns on both smooth and rough surfaces. The method is based on, and takes advantage of, the fact that high frequency spatial Fourier components are formed when a Gaussian profile beam interacts with an irregular, or otherwise inhomogeneous, surface. Through the measurement of these non-Gaussian components of the reflected beam, information about the sample surface may be obtained. An apparatus based on this principle comprises a light source [12] for producing a beam of light [10] directed along an optical path; a spatial filter [34], positioned along the optical path downstream from the light source, for giving the beam of light a Gaussian intensity profile [18]; positioning means [22] for positioning the material [20] in the optical path downstream from the spatial filter [34]; an inverse spatial filter [40], positioned along the optical path downstream from the material, for removing from the beam a Gaussian intensity profile; and a detector [46], positioned along the optical path downstream from the inverse spatial filter, for detecting the beam.

8 Claims, 5 Drawing Sheets

FIG. 1a
FIG. 1b
FIG. 1c
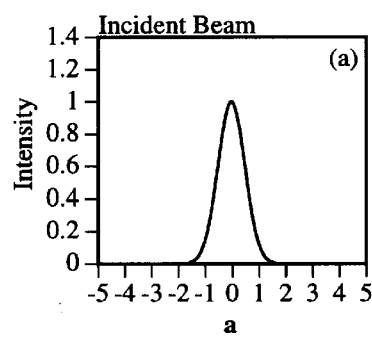
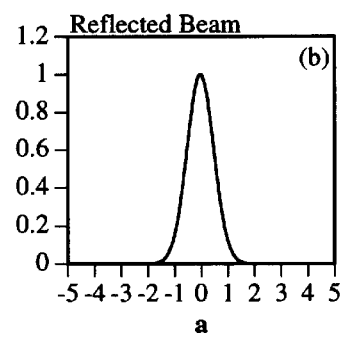
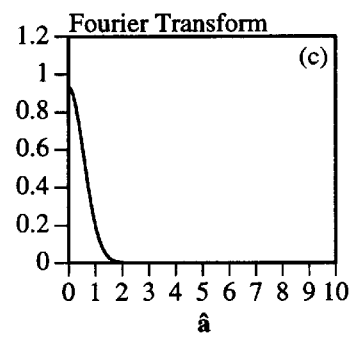

FIG. 3a
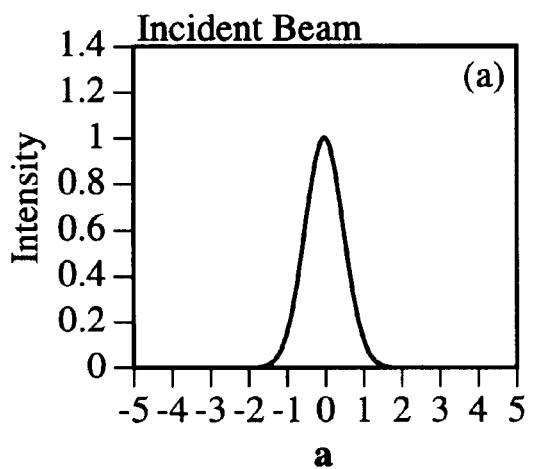
FIG. 3b
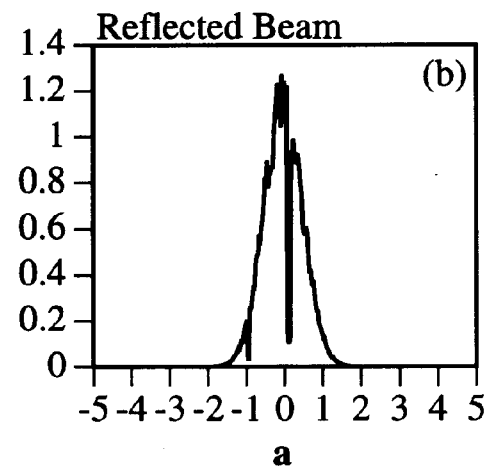
FIG. 3c
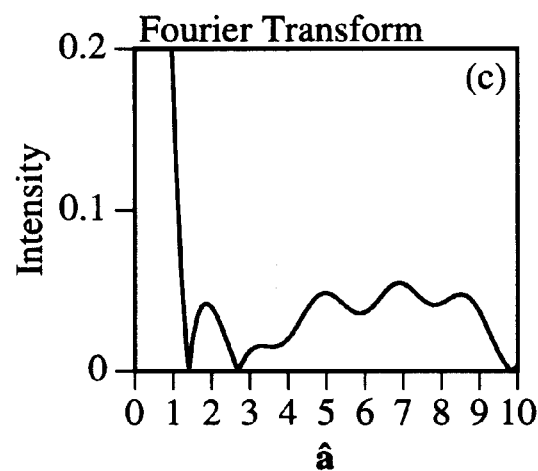
FIG. 3d

SURFACE ANALYSIS USING GAUSSIAN BEAM PROFILES

CROSS-REFERENCE TO RELATED APPLICATIONS

This application claims priority from U.S. Provisional Patent Application Ser. No. 60/045,672 filed May 6, 1997, which is incorporated herein by reference.

FIELD OF THE INVENTION

This invention relates generally to the surface characterization of materials, and, more specifically, to the measurement of surface roughness, the detection of minute particulate contaminants, and reconstruction of patterns on the surface of semiconductor wafer samples.

BACKGROUND OF THE INVENTION

As component densities in integrated circuit technology continue to increase, it becomes vitally important to possess an effective means of detecting the presence of sub-micron (i.e. less than $10^{-6}$ m) particulate contaminants on both patterned and unpatterned surfaces. The length scale of the patterned lines which comprise the basic elements of modern integrated circuits is rapidly approaching a level such that a particle which is on the order of 0.2 $\mu$m will completely disrupt the operation of the circuit. With today's technology, particulate detection at the 0.1 $\mu$m level is adequate for most purposes.

Known techniques for the detection of particulates on the surface of semiconductor wafer samples consist of either imaging or non-imaging techniques. In general, the imaging methods detect the presence of defects on patterned wafers by comparing the diffraction pattern of the image to a known diffraction pattern using a Fourier lens assembly. Defects appear as the differences between the known pattern and the diffraction pattern from the sample. These methods, however, are only useful for detecting contaminants on patterned surfaces. The nonimaging methods construct surface "images" by measuring some characteristic of the sample surface (e.g. the average surface roughness). Because these methods do not image the sample directly, they are primarily used in the characterization of unpatterned samples.

U.S. Pat. No. 5,189,481 describes a method and apparatus for detecting particulate contaminants on an unpatterned surface using a Coblentz sphere light detection assembly. In this method, light incident from the laser is focused on the sample surface. If there are particulate contaminants on the surface of the wafer, the incident photons will be diffusely reflected. The diffusely reflected light is then collected by the Coblentz sphere assembly and focused onto a detector. The intensity of the light on the detector is proportional to the number of particulate contaminants in the probe beam, or the total integrated scatter from the surface of the material. This method is not an imaging technique, so it cannot discriminate between a particulate contaminant and a rough sample surface.

U.S. Pat. No. 4,334,780 describes a method and apparatus for measuring the average surface roughness on an unpatterned surface by taking advantage of the diffusely reflecting properties of a "Gaussian rough surface". In this method, a collimated beam of light is reflected from a Gaussian rough surface and the spatial intensity distribution of the beam is subsequently measured by an imaging detector. The spatial distribution of the reflected beam can be associated with the average surface roughness of an ideal Gaussian reflecting surface. This method is not an imaging technique, so it cannot discriminate between a particulate contaminant and a rough sample surface. In addition, it cannot be used on patterned samples.

U.S. Pat. No. 3,614,232 describes a method for imaging defects in a patterned surface through the use of spatial filters. In this method, the incident beam of light is passed through a photomask which possesses the "defect free" diffraction pattern of an ideal patterned surface. When the photomask and the pattern on the sample are aligned properly, the only light which can reach the detector comes from defects in the pattern on the surface of the sample. In this way, defects on a patterned surface can be easily imaged. This method, however, requires that the diffraction pattern of the patterned surface be known, and that there be precise alignment between the photomask and the sample. In addition, this method of defect detection can only be used on patterned surfaces.

Various other U.S. patents use the diffraction properties of a patterned surface, and a unique spatial filter, to image defects on a sample surface. U.S. Pat. No. 4,330,775, for example, describes an apparatus which uses the differences in the diffraction patterns of a photomask and a patterned sample to detect defects on the sample. In addition, the sample is illuminated with incoherent light so that the image of the sample may be obtained simultaneously. U.S. Pat. Nos. 4,299,443, 4,806,774, 5,155,372, 5,172,000, 5,506,676, 5,659,390, and 5,719,405 all describe methods and instruments which detect defects in a repetitive pattern on a sample surface through the use of specific spatial filters matched to the pattern. All of these methods require the use of a unique spatial filter to detect defects in the unique pattern on the sample, and cannot be used to image particulates on unpatterned samples.

In short, the known methods of particle detection suffer from one or more of the following disadvantages: they are limited to the detection of particles on patterned surfaces, they are not sensitive to sub-micron size particles, they cannot discriminate between particulate contamination and surface roughness, and/or they require precise knowledge and matching of a surface pattern with a mask pattern,

SUMMARY OF THE INVENTION

Accordingly, it is an object of the present invention to provide a method for the characterization of a surface that is able to:

(1) detect sub-micron size particles, (2) image both patterned and unpatterned surfaces, and (3) distinguish particulate contamination from surface roughness.

These objects and advantages are attained by a new method for measuring the physical characteristics of reflective or transparent surfaces. In various manifestations, the method may be used to detect particulates, measure surface roughness, and reconstruct surface images and detect defects in regular patterns on both smooth and rough surfaces. The method is based on, and takes advantage of, the fact that high frequency spatial Fourier components are formed when a Gaussian profile beam interacts with an irregular, or otherwise inhomogeneous, surface. The present inventor has recognized that through the measurement of these non-Gaussian components of the reflected beam, information about the sample surface may be obtained.

In one aspect of the invention, an apparatus is provided for detecting surface properties of a material. The apparatus comprises a light source for producing a beam of light directed along an optical path; a spatial filter, positioned along the optical path downstream from the light source, for giving the beam of light a Gaussian intensity profile; positioning means for positioning the material in the optical path downstream from the spatial filter; an inverse spatial filter, positioned along the optical path downstream from the material, for removing from the beam a Gaussian intensity profile; and a detector, positioned along the optical path downstream from the inverse spatial filter, for detecting the beam.

In a preferred embodiment of the apparatus, the spatial filter comprises a first Fourier lens assembly and a circular aperture positioned in the focal plane of the first Fourier lens assembly. In addition, the inverse spatial filter comprises a second Fourier lens assembly and an opaque circular disk positioned in the focal plane of the second Fourier lens assembly.

In another aspect of the invention, a method is provided for detecting surface properties of a material. The method comprises producing a beam of light; spatial filtering the beam of light to produce spatially filtered beam having a Gaussian intensity profile; causing the spatially filtered beam to interact with the material to produce a distorted beam; inverse spatial filtering the distorted beam to produce an inverse spatially filtered beam having a Gaussian intensity profile removed; and detecting the inverse spatially filtered beam.

In a preferred embodiment of the method, the spatial filtering comprises passing the beam of light through a circular aperture positioned in the focal plane of a first Fourier lens assembly, and the inverse spatial filtering comprises passing the distorted beam through an opaque circular disk positioned in the focal plane of a second Fourier lens assembly. In one implementation of the method, the spatially filtered beam interacts with the material by reflecting from a surface of the material. In another implementation, the spatially filtered beam interacts with the material by transmission through material.

BRIEF DESCRIPTION OF THE DRAWINGS

FIG. 1a shows the spatial intensity profile of a beam having a Gaussian profile, in accordance with the teaching of the invention.

FIG. 1b shows the intensity profile of the beam of FIG. 1a after reflection from a clean, specular surface, in accordance with the teaching of the invention.

FIG. 1c shows the Fourier transform of the beam of FIG. 1b, in accordance with the teaching of the invention.

FIG. 3a shows the spatial intensity profile of a beam having a Gaussian profile, in accordance with the teaching of the invention.

FIG. 3b shows the spatial intensity profile of the beam of FIG. 3a after reflection from a rough surface contaminated with particulate defects, in accordance with the teaching of the invention.

FIG. 3c shows the Fourier transform of the beam of FIG. 3b, in accordance with the teaching of the invention.

FIG. 3d shows the difference image beam obtained by inverse spatial filtering the beam of FIG. 3c, in accordance with the teaching of the invention.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention. The principle at the basis of the surface characterization method of the present invention is illustrated in FIGS. 1 to 3. FIG. 1a shows the intensity distribution of a spatially "pure" laser beam, i.e. a beam having a Gaussian intensity profile. For simplicity of illustration the figures show only one dimension of the beam profile. This intensity profile is plotted in units of the beam radius, a. After reflection from a "clean", specular surface, the beam retains its original Gaussian profile as shown in FIG. 1b. The Fourier transform (FT) of this beam can be obtained by passing the beam through a Fourier lens. The spatial FT of the reflected beam will be in the focal plane of this lens. It is well known that the Fourier transform of a Gaussian function is also a Gaussian function. This is illustrated in FIG. 1c which depicts the FT of the Gaussian beam profile shown in FIG. 1b, in units of a, where a is equal to $(\lambda.f)/(\pi a)$, with $\lambda$ equal to the wavelength, and f equal to the focal length of the lens. It is easily seen in FIG. 1c, that for values of â above approximately 2, there are no Fourier components. Thus, the Gaussian components of the reflected beam can be largely removed with a spatial filter in the focal plane of the Fourier lens. A spatial filter consisting of a circle of radius 2â will remove 99.97% of the light from the original Gaussian beam. In this case, because the reflecting surface is free of contaminants, the spatial filter removes virtually all of the light from the reflected beam.

Figure 2A:
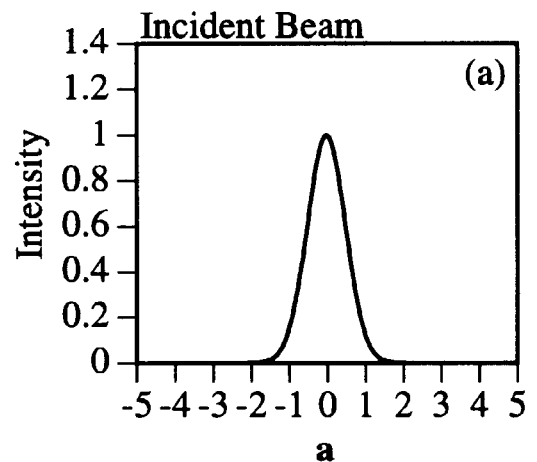
FIG. 2a shows the spatial intensity profile of a beam having a Gaussian profile, in accordance with the teaching of the invention.
Figure 2B:
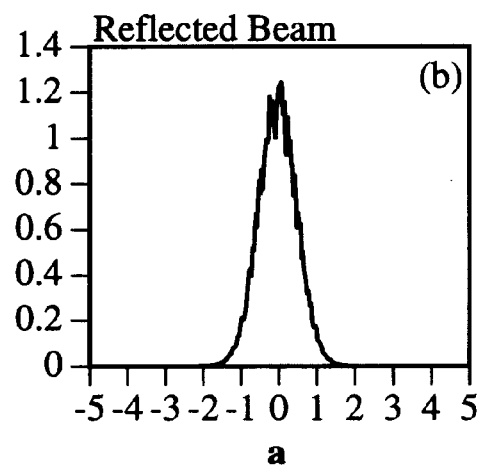
FIG. 2b shows the spatial intensity profile of the beam of FIG. 2a after reflection from a rough surface, in accordance with the teaching of the invention.
Figure 2C:
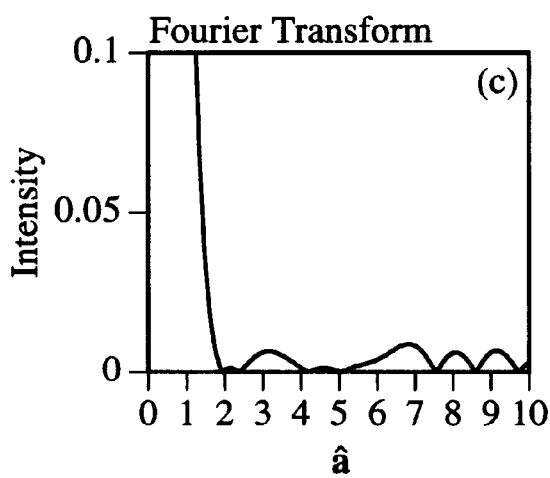
FIG. 2c shows the Fourier transform of the beam of FIG. 2b, in accordance with the teaching of the invention.
Figure 2D:
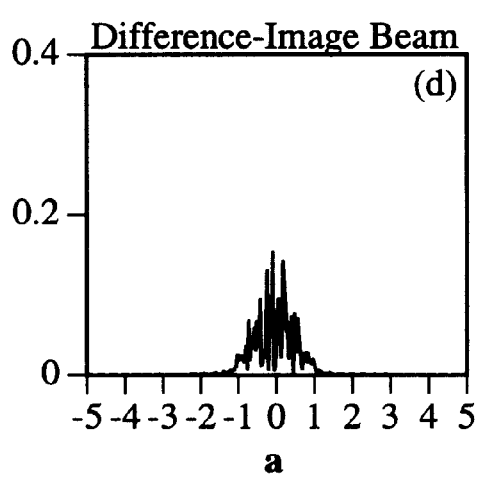
FIG. 2d shows the difference image beam obtained by inverse spatial filtering the beam of FIG. 2c, in accordance with the teaching of the invention.

If an incident laser beam with a Gaussian profile is focused on a sample with a rough surface, then the spatial profile of the reflected beam will deviate from the original Gaussian profile due to the diffuse scattering caused by the rough surface. This is illustrated in FIGS. 2a, 2b, 2c, 2d. The reflected beam profile, FIG. 2b, is seen to be distorted from the original Gaussian form, FIG. 2a, by the surface roughness. The spatial FT of this reflected beam is shown in FIG. 2c where it is seen that there are now significant high-â Fourier components in the beam profile. By removing the Gaussian profile contribution to the beam using a 4â diameter circular spatial filter, and inverse Fourier transforming the beam with a second Fourier lens, the resulting non-Gaussian difference-image beam profile will be incident on the detector. This beam profile is shown in FIG. 2d, and is seen to closely resemble the noise distribution from the reflected beam. In this example, the signal on the detector will then be proportional to the amount of diffusely reflected light and thus to the degree of surface roughness on the sample.

If a Gaussian beam is reflected off a rough surface with particulate contaminants whose dimensions are smaller than the beam size, then it is possible to discriminate between the scattering due to surface roughness and the scattering due to the contaminant particles. This process is illustrated in FIGS. 3a, 3b, 3c, 3d. The incident Gaussian beam, FIG. 3a, is reflected off a rough, contaminated surface with two particles located at approximately −1a and 0a, within the beam spot. The reflected beam will contain the resulting deviations in the beam profile caused by the presence of both the surface roughness and the particulate contaminants, as shown in FIG. 3b. By Fourier transforming the reflected beam profile (FIG. 3c), and then spatially filtering out the Gaussian components of the beam, the resulting FT difference-image beam may be measured with an appropriate imaging detector such as a charge coupled device (CCD) array. This image will depict both the surface roughness of the sample and the localized particulate as shown in FIG. 3d. Thus, by collecting the difference-image of the beam with a CCD array, it is possible to discriminate between scattering from a uniformly rough surface and from a localized particle.

In general, this method uses the differences in the spatial profile of a reflected Gaussian laser beam to determine the surface properties of a material. These differences can be measured by removing the Gaussian components of the incident beam with an appropriate Fourier lens and spatial filter assembly.

Figure 4:
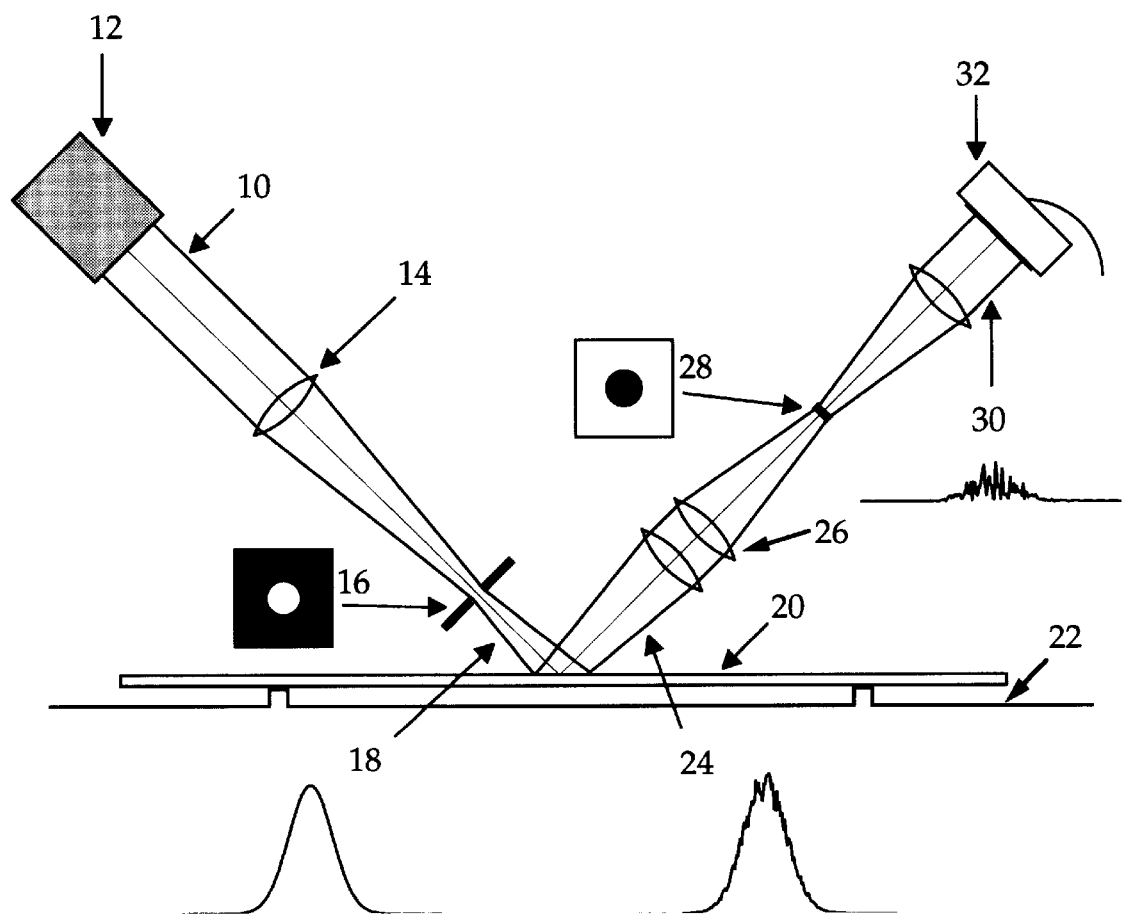
FIG. 4 is a schematic diagram of an apparatus according to one embodiment of the present invention.

An example optical configuration of an instrument designed to measure the surface roughness of a sample through a measure of the total integrated scatter is shown in FIG. 4. Note that although the following description of a preferred embodiment illustrates the case where the beam is reflected from the surface of a sample, it will be appreciated that the principles of the invention apply to the case of transmission as well as reflection.

In the configuration shown in FIG. 4, a collimated light beam 10 from a laser 12 is spatially filtered by a Gaussian filter assembly comprising a Fourier lens 14 and an aperture 16. The spatial filtering results in a "clean" Gaussian beam profile 18 which then reflects off a surface of a sample 20 at angle equal to the angle of incidence (45° in this example). The sample 20 is positioned relative to the device optics by any of various well known techniques. For example, the sample may be placed at rest on a wafer stand 22 moved or positioned relative to the device optics. Those skilled in the art will appreciate that any known techniques for positioning and moving samples relative to optical devices will be directly applicable to the present situation. The reflected beam, which typically has a distorted profile 24 due to the interaction with the surface, is then inverse spatially filtered with a Fourier lens 26 and a spatial inverse of the pinhole filter, i.e. an opaque disk 28. This spatial filtering removes the majority of the Gaussian components (99.97%) from the profile of the reflected beam, resulting in a difference image beam profile 30. The intensity of the difference-image beam is then measured with a detector 32. The detector can measure the total integrated scatter of the sample surface with an integrating detector (photodiode, photomultiplier, etc.) or collect the difference-image of the sample with a CCD imaging array or the like.

It will be appreciated that many different configurations may be constructed which may take advantage of this method. For example, The angle of incidence of the laser beam may be varied from near-normal incidence to grazing incidence without affecting the operation of the instrument in any significant way. The optical layout of the instrument is determined primarily through engineering convenience and designed to achieve the maximum optical throughput.

Figure 5:
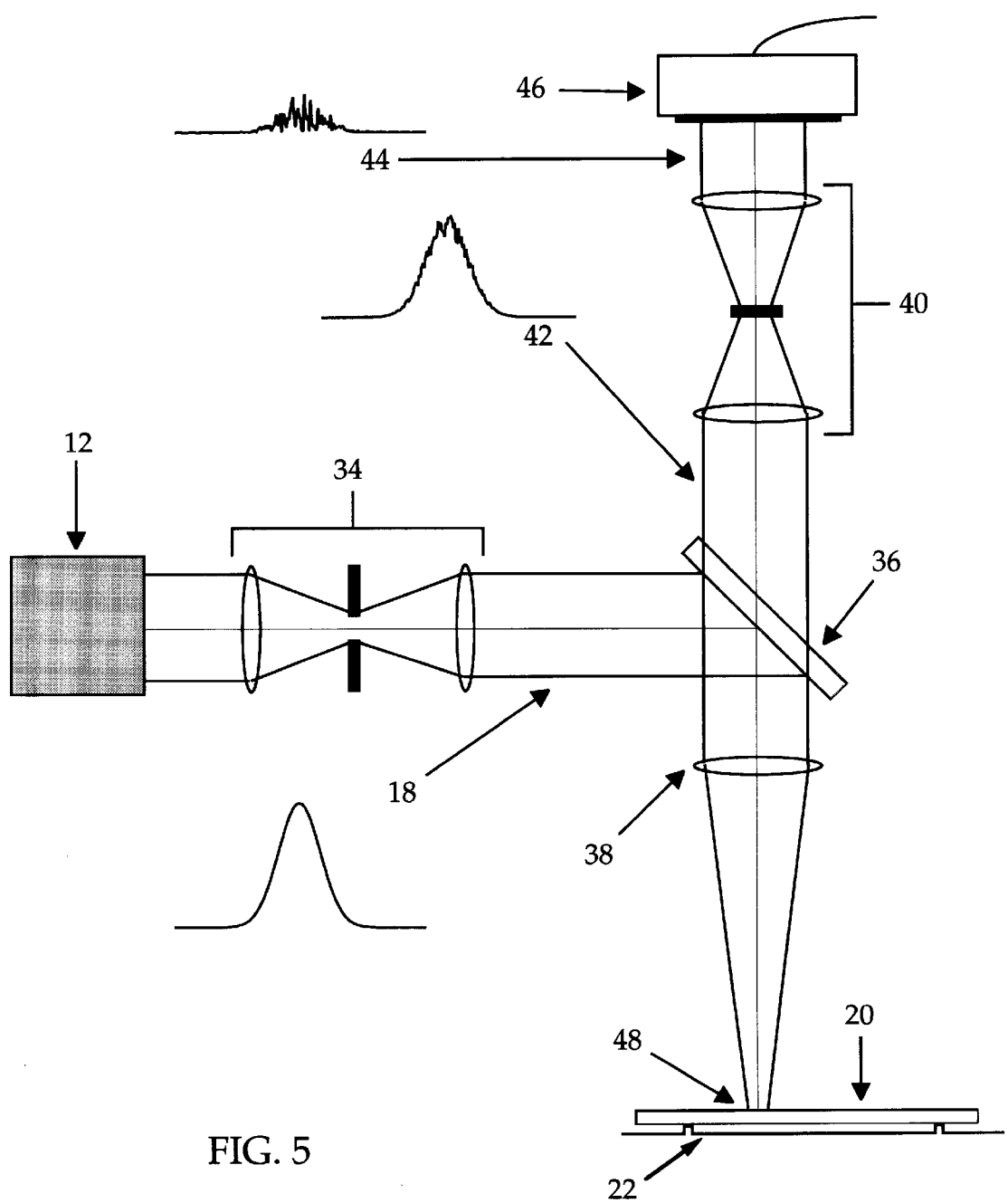
FIG. 5 is a schematic diagram of an apparatus according to an alternative embodiment of the present invention.

This typically will result in incident angles less than 45° from the normal. An alternative optical configuration is shown in FIG. 5. In this configuration a collimated beam 10 from a laser 12 is spatially filtered using a Gaussian filter assembly 34 comprising an aperture and Fourier lens, analogous to the embodiment shown in FIG. 4. After passing through the Gaussian filter assembly, the spatially filtered beam 18 is directed toward the surface of the sample by a 50/50 beam splitter 36 and focused by a focusing lens 38 onto a sample 20 at normal incidence. The reflected beam then passes through the 50/50 beam splitter 36 and is inverse spatially filtered by a second Gaussian filter assembly 40 containing an inverse spatial filter, analogous to the embodiment shown in FIG. 4. The inverse spatially filtering removes the Gaussian components of the reflected beam profile 42. The resulting Difference-Image beam profile 44 is then measured with either an integrating or a spatially resolving detector (i.e. a CCD array) 46. By focusing the laser beam to a small spot 48 using the focusing lens 38, this embodiment provides increased sensitivity to the presence of smaller particles on the surface of the sample because the particle size will be larger with respect to the beam size. This design also has the advantage of being very compact. The entire probe instrument may be constructed to measure less than approximately 6 cm on a side.

Following is a detailed description of components which may be used to construct the devices described above, as well as various design considerations. Note that this list is not unique, and that other optical configurations can be assembled based upon the principles of the present invention, the specific engineering requirements of the instrument, and the property of the surface to be measured.

Light Source

The light source 12 used in the preferred embodiment is a laser diode (Item #97002-063) available from ThorLabs, Inc. This compact visible laser diode module has an approximate lifetime of 100,000 hours. The laser emits a 3 mm diameter circular beam with a 0.3 mRad divergence at 670 nm. This is a 1.0 mW class II laser.

Spatial Filter Assembly (Gaussian Filter)

The Spatial Filter Assembly 34 consists of three components; two Fourier lenses and a pinhole filter. The lenses are available from NewPort Corporation. They are bi-convex optical glass lenses with anti-reflection coatings suitable for 670 nm light. Item KBX013 with a focal length of 12.7 mm and a diameter of 6.35 mm is adequate for this application. This lens selection will determine the optics for the rest of the instrument as well as the dimension of the spatial filters and the working distance of the sample probe beam.

The layout of the Spatial Filter Assembly is as follows. The two lenses are positioned 25.4 mm (2f) apart and are separated by a spatial pinhole filer. The optimum diameter, $D_{opt}$, of the pinhole filer can be calculated from $D_{opt} = f \lambda / a$, where $\lambda$ is the laser wavelength, f is the focal length of the bi-convex lens, and a is the input beam radius. With $\lambda = 670$ nm, f=12.7 mm and a beam radius of 1.5 mm, the optimum pinhole filter diameter is ~5.6 μm. The selection of the pinhole filter 16 is determined by the availability of commercial filters using the value of $D_{opt}$ as the minimum radius. With these constraints, a 10 μm pinhole filter will be adequate for this application. This filter is item PH-10 available from Newport Corporation.

50/50 Beam Splitter

A dichroic cube beam splitter 36 available from Edmund Scientific Co. can be used to split the filtered laser beam into two beams. The intensities of the reflected and transmitted beams with these splitters approach 50% of the input beam.

Note, the use of this component in the optical path will result in a maximum 25% throughput of the input beam (50% reflected multiplied by 50% transmitted) assuming the sample has a reflectivity near unity.

The beam transmitted through the 50/50 beam splitter parallel to the incident beam from the laser is removed by a highly absorbing beam stop positioned just beyond the beam splitter. The BLACKHOLE™ laser beam trap available from ThorLabs, Inc. is suitable for this application.

Focusing Lens

The focusing lens 38 is the same as those used to spatially filter the input laser beam. The bi-convex lens has a focal length of 12.7 mm and a diameter of 6.35 mm. The f/# of this lens is 2.0. The spot size at the focus can be calculated from the beam waist equation with $w_0=(2\lambda/\pi)$ (f/#). The diameter of the spot on the sample in this configuration is approximately 0.85 $\mu$m. The depth-of-focus (DOF) in this configuration can be calculated from, $DOF=(8\lambda/\pi)$ $(f/\#)^2$. This configuration has a DOF equal to approximately 7 $\mu$m.

These values for the spot size and the depth-of-focus may easily be varied by replacement of this lens with another which possesses a different focal length and f/#. The final design may depend on the specific characteristics of the sample which are being measured.

Spatial Filter Assembly (Gaussian Removal Filter)

This spatial filter 40 has the same design as the filter assembly used to filter the input Gaussian beam. The only difference is that the spatial filter is now an opaque circle 28 of radius 6 $\mu$m which will remove the Gaussian components of the beam from the reflected probe beam. This filter can be made using standard microfabrication techniques (i.e. photolithography).

Detector

The detector 46 may comprise either a CCD array, or an integrating detector such as a silicon photodiode or a photomultiplier. These detectors are available from a variety of commercial sources in a wide range of sizes. Possible detector sources include; ThorLabs, Inc., Oriel Corporation, Edmund Scientific Company, Newport, and New Focus, Inc.

It will be clear to one skilled in the art that the above embodiments may be altered in many ways without departing from the scope of the invention. Accordingly, the scope of the invention should be determined by the following claims and their legal equivalents.

What is claimed is:

1. An apparatus for detecting surface properties of a material, the apparatus comprising:
   a) a light source for producing a beam of light directed along an optical path;
   b) a first spatial filter, positioned along the optical path downstream from the light source, for giving the beam of light a Gaussian intensity profile;
   c) positioning means for positioning the material in the optical path downstream from the first spatial filter;
   d) a second spatial filter, positioned along the optical path downstream from the material, for removing from the beam a Gaussian intensity profile, wherein the second sipatial filter is a spatial inverse of the first spatial filter; and
   e) a detector, positioned along the optical path downstream from the second spatial filter, for detecting the beam.

2. The apparatus of claim 1 wherein the first spatial filter comprises a first Fourier lens assembly and a circular aperture positioned in the focal plane of the first Fourier lens assembly.

3. The apparatus of claim 1 wherein the second spatial filter comprises a second Fourier lens assembly and an opaque circular disk positioned in the focal plane of the second Fourier lens assembly.

4. A method for detecting surface properties of a material, the method comprising the steps of:
   a) producing a beam of light;
   b) spatial filtering the beam of light to produce spatially filtered beam having a Gaussian intensity profile;
   c) causing the spatially filtered beam to interact with the material to produce a distorted beam;
   d) inverse spatial filtering the distorted beam to produce an inverse spatially filtered beam having a Gaussian intensity profile removed, wherein the inverse spatial filtering is a spatial inverse of the spatial filtering; and
   e) detecting the inverse spatially filtered beam.

5. The method of claim 4 wherein the spatial filtering comprises passing the beam of light through a circular aperture positioned in the focal plane of a first Fourier lens assembly.

6. The method of claim 4 wherein the inverse spatial filtering comprises passing the distorted beam through an opaque circular disk positioned in the focal plane of a second Fourier lens assembly.

7. The method of claim 4 wherein causing the spatially filtered beam to interact with the material comprises reflecting the spatially filtered beam from a surface of the material.

8. The method of claim 4 wherein causing the spatially filtered beam to interact with the material comprises transmitting the spatially filtered beam through the material.

* * * * *